US012567505B2

(12) United States Patent
Clark

(10) Patent No.: US 12,567,505 B2
(45) Date of Patent: Mar. 3, 2026

(54) SYSTEM THAT SELECTS AN OPTIMAL MODEL COMBINATION TO PREDICT PATIENT RISKS

(71) Applicant: NIHON KOHDEN DIGITAL HEALTH SOLUTIONS, LLC, Irvine, CA (US)

(72) Inventor: Matthew Clark, Afton, VA (US)

(73) Assignee: NIHON KOHDEN DIGITAL HEALTH SOLUTIONS, LLC, Irvine, CA (US)

( * ) Notice: Subject to any disclaimer, the term of this patent is extended or adjusted under 35 U.S.C. 154(b) by 277 days.

(21) Appl. No.: 17/686,559

(22) Filed: Mar. 4, 2022

(65) Prior Publication Data

US 2023/0282356 A1 Sep. 7, 2023

(51) Int. Cl.
 *G06Q 10/00* (2023.01)
 *G16H 50/20* (2018.01)
 *G16H 50/30* (2018.01)

(52) U.S. Cl.
 CPC ............. *G16H 50/30* (2018.01); *G16H 50/20* (2018.01)

(58) Field of Classification Search
 CPC ............................... G16H 50/30; G16H 50/20
 See application file for complete search history.

(56) References Cited

U.S. PATENT DOCUMENTS

| | | | | | |
|---|---|---|---|---|---|
| 11,238,469 | B1 * | 2/2022 | Talvola | ................... | G06N 20/20 |
| 11,640,661 | B2 | 5/2023 | Washko et al. | | |
| 11,798,653 | B2 * | 10/2023 | Yu | ............................. | G06N 5/01 |
| 11,854,706 | B2 * | 12/2023 | Peri | ......................... | G06F 16/45 |
| 2020/0005940 | A1 | 1/2020 | Laschet et al. | | |
| 2021/0098090 | A1 * | 4/2021 | Thomas | .................. | G16H 50/30 |
| 2021/0233241 | A1 * | 7/2021 | Washko, Jr. | ........... | G16H 30/40 |
| 2021/0342757 | A1 * | 11/2021 | Yu | ............................. | G06N 7/01 |

OTHER PUBLICATIONS

International Search Report and Written Opinion issued in PCT/US23/14660 on May 25, 2023 (9 pages).
International Preliminary Report on Patentability issued in PCT/US23/14660 on Sep. 19, 2024.

* cited by examiner

*Primary Examiner* — Rajesh Khattar
(74) *Attorney, Agent, or Firm* — ARC IP Law, PC; Joseph J. Mayo

(57) ABSTRACT

An automated system that selects an optimal combination of risk models for a target patient population. The selected combination may be monitored by clinicians to determine which patients are at greatest risk for adverse events or clinical deterioration. The system may compare risk model data for hundreds or thousands of models to data collected on a target patient population to determine which combination of models is the best fit for this target group. An illustrative selection method may minimize a cost function that measures the deviation between a model combination and desired features for an optimal combination. Illustrative factors in the cost function may include differences between the predicted risk distributions for the target group, using the model risk function, and the risk distributions for the dataset used to train the model, and correlation among risks predicted by the models in the combination.

17 Claims, 11 Drawing Sheets

| Model Event | Physiological System(s) |
|---|---|
| Intubation | Respiratory |
| Hemorrhage | Cardiovascular |
| Sepsis | Respiratory, Cardiovascular |
| Hypoglycemia | Endocrine |
| ... | ... |

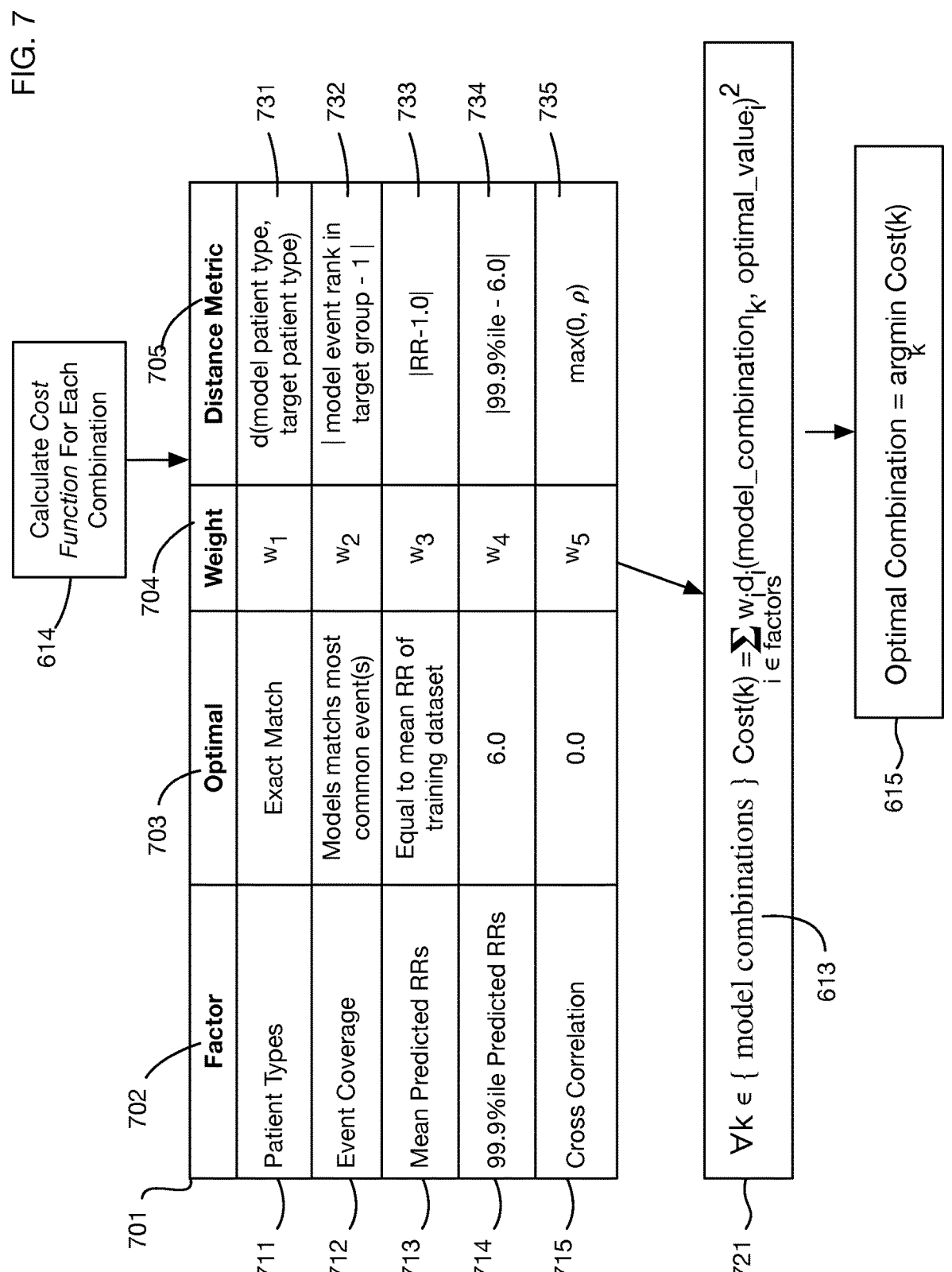

614 — Calculate *Cost Function* For Each Combination

| Factor | Optimal | Weight | Distance Metric |
|---|---|---|---|
| Patient Types | Exact Match | $w_1$ | d(model patient type, target patient type) |
| Event Coverage | Models matchs most common event(s) | $w_2$ | \| model event rank in target group - 1 \| |
| Mean Predicted RRs | Equal to mean RR of training dataset | $w_3$ | \|RR-1.0\| |
| 99.9%ile Predicted RRs | 6.0 | $w_4$ | \|99.9%ile - 6.0\| |
| Cross Correlation | 0.0 | $w_5$ | $max(0, \rho)$ |

701    702    703    704    705

711   712   713   714   715

731   732   733   734   735

$$\forall k \in \{\text{ model combinations }\} \quad Cost(k) = \sum_{i \in factors} w_i \cdot d_i (model\_combination_k, \ optimal\_value_i)^2$$

613

$$\text{Optimal Combination} = \underset{k}{argmin} \ Cost(k)$$

615

Event Type Distance Metric —— 732

Models

SYSTEM THAT SELECTS AN OPTIMAL MODEL COMBINATION TO PREDICT PATIENT RISKS

BACKGROUND OF THE INVENTION

Field of the Invention

One or more embodiments of the invention are related to the field of health care information systems and medical devices. More particularly, but not by way of limitation, one or more embodiments of the invention enable a system that selects an optimal model combination to predict patient risks.

Description of the Related Art

Many risk prediction models have been developed, and continue to be developed and refined, to predict the risks of certain adverse events occurring for individual patients in a patient population. For example, a sepsis model may predict the risk that a patient develops sepsis in the next 24 hours, based on analyses of the patient's vital signs, labs, and demographics. Medical professionals may use these models to determine which patients are at greatest risk for which events, and to adjust the care of these patients accordingly. A challenge faced by health care facilities is that so many different models exist that it is impractical to use or monitor all of them simultaneously. Similarly, although multiple models may exist for predicting the future risk of the same acute illness, determining the best model for a given population without collecting an independent data set or conducting a clinical study is difficult.

Ideally each patient care team would monitor a relatively small number of risk prediction models to assess the most critical risks for patients in the patient population served by that team. Currently the only available approach for selecting risk prediction models is to iteratively experiment with different models to find those that are effective for each environment. This approach requires the additional step of monitoring patient events through time and is time consuming and is impractical when new risk prediction models are constantly being developed. There are no known systems that automatically analyze the characteristics of a target patient group to suggest an optimal combination of risk prediction models for that patient group.

For at least the limitations described above there is a need for a system that a selects an optimal model combination to predict patient risks.

BRIEF SUMMARY OF THE INVENTION

One or more embodiments of the invention may enable a system that selects an optimal model combination to predict patient risks. The system may automatically compare combinations of many models to characteristics of a target patient group to determine the optimal combination for this group.

One or more embodiments of the invention may include multiple risk models, data on a target patient group, and a processor that analyzes the risk model data and the target patient group data to automatically select an optimal model combination for the target patient group. Each risk model may be associated with: an event, one or more physiological systems associated with the event, a patient type, one or more inputs, a function that maps values of the inputs to a probability of occurrence of the event for patients of the model's patient type, and training samples, each with training sample input values and a training sample output value that is the occurrence of the event for that sample. Target patient group data may include the target patient type, target patient clinical acuity, the target patient available inputs, and target patient samples with sample input values for the target patient available inputs. The processor may select an optimal model combination for the target patient group using the following steps: The multiple models may be filtered to identify a set of applicable risk models based on the target patient group data. The processor may receive (for example from an operator) a model combination cardinality (an integer greater than or equal to two) which is the desired number of models in the combination. The processor may generate all relevant combinations of the applicable risk models with the desired cardinality, and for which different models in each relevant combination have different associated physiological systems. A cost function may then be applied to each of the relevant combinations; this cost function measures differences between each combination and a theoretically optimal combination for the target patient group. The processor may then select the model combination with the lowest associated cost.

In one or more embodiments, the filter to select applicable risk models may ensure that the model inputs are included in the target patient available inputs, and that the target patient type contains the risk model patient type.

In one or more embodiments, the cost function may be a weighted sum of cost factors.

In one or more embodiments, the cost factors may include a predicted risk distribution difference factor for each model of a combination. This factor may be based on a difference between a distributional statistic of, or a statistic applied to a predicted target patient group risk distribution and a desired value of the statistic. Illustrative statistics may include for example, without limitation, a mean, a percentile, an entropy, an entropy rate, or a distribution divergence. The predicted target patient group risk distribution may be calculated by applying the model function to the target patient sample input values and dividing the result by the mean value of the training sample output values associated with the model.

In one or more embodiments the desired value of a risk distribution statistic may be the value of the statistic applied to the training set risk distribution, which is the distribution of the training sample output values divided by the mean value of these training sample output values. In one or more embodiments the mean value of the predicted risk distribution may be compared to the mean value of the training set risk distribution.

In one or more embodiments a cost factor may be based on the difference between the 99.9th percentile of the predicted target patient group risk distribution and a maximum value of a risk display range.

In one or more embodiments the cost factors may include an outputs correlation factor, which may be a correlation coefficient between the predicted target patient group risk distributions across the models in a combination.

In one or more embodiments the cost factors may include a patient type difference factor for each model in a combination, which is based on a difference between the model's patient type and the target patient group patient type.

In one or more embodiments the cost factors may include an event frequency factor for each model in a combination, which measures how frequently the model's event occurs in the target patient group data.

In one or more embodiments the cost factors may include an entropy estimate (at a relevant scale or multiscale) for each model in the combination, which may for example measure how smooth the model's predicted target patient group risk distribution is relative to the distribution of risks in the model's training set.

In one or more embodiments the cost factors may include an input distribution similarity factor that may for example compare distributions of individual features in the target patient sample input values to distributions of the same features in the model's training sample input values, for each model in the combination.

BRIEF DESCRIPTION OF THE DRAWINGS

The above and other aspects, features and advantages of the invention will be more apparent from the following more particular description thereof, presented in conjunction with the following drawings wherein:

FIG. 7 shows an illustrative cost function framework that may be applied to calculate an optimal model with a minimum cost, where the cost function measures the difference between a model combination and the desired characteristics.

DETAILED DESCRIPTION OF THE INVENTION

A system that a selects an optimal model combination to predict patient risks will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
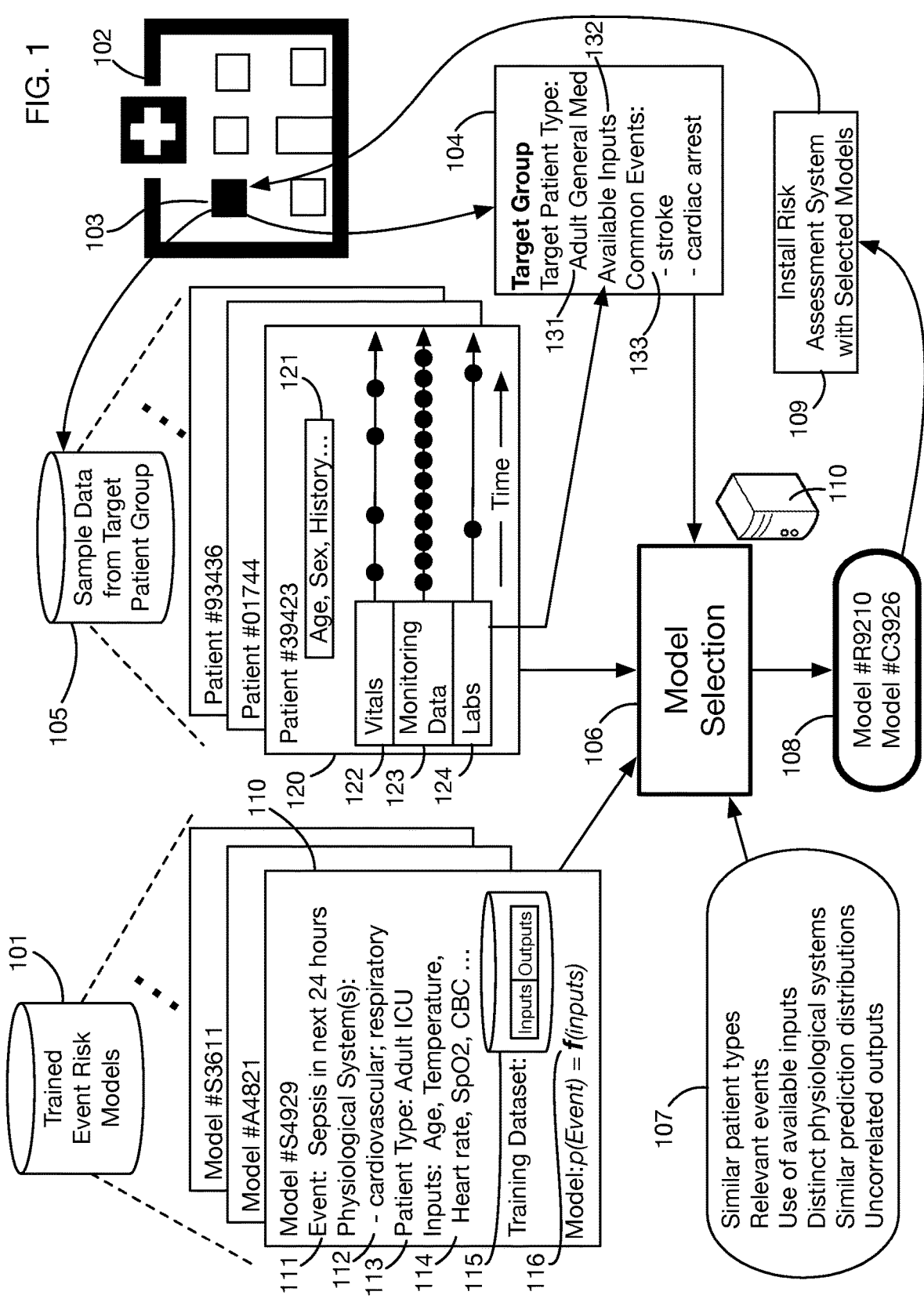
FIG. 1 shows an architectural diagram of an illustrative embodiment of the invention; a model selection system selects an optimal combination of risk prediction models for a target patient group based on sample data collected from target group.

FIG. 1 shows an architectural diagram of illustrative elements of one or more embodiments of the invention. In an illustrative scenario, an application administrator of a health care facility or similar organization 102 wants to install one or more risk prediction models for a target group of patients 103. This target patient group may be for example the patients in a specific unit of a hospital or similar facility, or it may be a group of similar patients that are treated in various locations. The target group of patients may be identified and grouped based for example on any or all of acuity, common procedures, demographic characteristics, etc.

A database 101 of risk models is available, and the organization 102 wants to use a combination of models from this database that best meets the needs of that target patient group. Because database 101 may contain hundreds or thousands of risk models, it is impractical to evaluate or try each model individually. Instead, automated model selection system 106 may be used to automatically analyze the models and the target patient group data 104 and 105 to recommend an optimal model combination 108 for the target patient group 103. Model selection system 106 may run on a processor 110, which may be for example, without limitation, a server, a desktop computer, a laptop computer, a notebook computer, a tablet computer, a mobile device, a CPU, a GPU, a co-processor, an ASIC, or a network of any number of any of these devices. The model selection system 106 may be coupled to database 101 and to data generated by or obtained from target patient group 103. After model selection system 106 generates recommended model combination 108, this combination or a variation thereof may be installed in step 109 in a risk assessment system for target patient group 103. This risk assessment system may for example continually or periodically monitor patients in the target group for the risks associated with each model in the selected multi-dimensional combination.

Because the model selection system is automated, the procedure shown in FIG. 1 may be repeated periodically or as needed as additional data is collected on the target patient group, or as the patient mix or health conditions in the target patient group shift over time. The comparisons and cost functions described below may also be used to monitor how well the selected model combination fits the target patient group over time.

FIG. 1 shows data associated with an illustrative risk model 110 in risk model database 101. Each risk model may predict the probability (i.e., risk) of a particular event (or the probabilities of multiple events) occurring over a specified timeframe, for example. The event 111 associated with illustrative model 110 is the development of sepsis in a patient within the next 24 hours. Events may be associated for example with the development, change, or resolution of clinical conditions; with the need for interventions such as intubation; or with other changes in patient state such as transfer to an ICU or discharge from a hospital. A model may predict the probability of any type of event or types of events that may affect or reflect patient care or patient condition. A model may be associated with any timeframe over which the probability of event occurrence is predicted. The physiological systems 112 associated with model 110 are the systems that are related to event 111 of sepsis. Each model may be associated with one or more physiological systems that are related to the model's event.

Some models may be applicable to certain patient populations or illness acuity, which may be related for example to patient demographics, patient conditions, patient treatments, or any other factors that define a group of patients. For example, some models may apply only to pediatric patients, and others may apply only to adult patients. In some situations, these patient populations may correspond to a type of care unit that treats patients of this type. A patient population for a model may be defined based on any combinations of factors such as patient age or other demographics, admitting diagnoses, acuity/illness severity, and N-dimensional distributions of laboratory measurements, vital signs, and other physiological data.

Model 110 is associated with a patient type 113 of adult patients that require intensive care, who may be treated for example in an intensive care unit. The model risk prediction for event 111 is therefore optimized for patients in this type of unit or with this type of acuity. The patient group type associated with a model may have any level of granularity; for example, some models may be associated with adult patients in general, while others may be associated with very specific patient groups such as patients in an Adult Cardiac Surgery unit.

Each model calculates event probabilities from a set of input data, such as patient demographic information, lab results, nursing vital signs, bedside measurements, and calculated features based on any of this information. Calculated features may be designed to enhance the representation of the change in a variable through time or may better represent information embedded in the time series of measurements, waveform shape and morphology and the signature of developing illness as represented in a combination of variables. Model 110 has associated input data 114, which is the set of inputs used to calculate the probability of sepsis occurring in the patient. Different models may use different sets of input data. Each model also has an associated function 116 that calculates the probability of the event (or events) of the model occurring from the input values 114. This function may for example be derived using machine learning methods applied to a training dataset 115 with input/output data that may be obtained from similar patient populations. For example, for model 110, training dataset 115 may be obtained by collecting input data 114 and output data that labels each patient based on whether that patient developed sepsis during a 24-hour period. Models may use any type or types of machine learning methods, such as for example, without limitation, regression, restricted cubic spine regression, neural networks, decision trees, bagged or boosted decision trees, and ensembles of models that use any of these methods.

Model selection system 106 compares data on each model to the characteristics of the target patient group 103 to determine an optimal model combination 108. Target patient group characteristics may include information 104 that is known about the target patient group prior to the model selection process. In the example shown in FIG. 1, it is known that the patient type 131 of target patient group 103 is Adult General Medicine. In some situations, the target patient group type may be known with great specificity, while in other situations the target group may include a mix of patient types, or the specific types of patients may be unknown. Target patient group data 104 may also include information 132 on the available inputs for this patient group, such as the clinical or demographic data that is collected for these patients. In some situations, there may also be available data 133 on the most common events of interest that occur in the target patient group, which may be determined for example by a review of target patient medical records or by interviewing staff.

In one or more embodiments, sample patient data 105 may be collected from the target patient group 103 over some period of time, such as a month, and this data may also be used in the model selection process. Data for illustrative patient 120 from the target patient group may include for example demographic and medical history information 121, flow sheet entries and clinical assessments (such as Glasgow comma score), vital signs 122 obtained for the patient over time (such as blood pressure, temperature, etc.), monitoring data 123 from bedside monitoring instruments such as heart monitors, parameters and waveforms from ventilators, EEG waveforms, and lab results 124. This data corresponds to the available inputs 132 that are associated with the target patient group. This data is illustrative, and one or more embodiments may collect any types of information related to the patient's condition, identity, history, or treatment. Data from a sample set of patients from the target patient group 103 may be collected over the desired time period and this dataset 105 may be input into the model selection system 106.

The model selection system 106 may select an optimal model combination 108 based on a set of objectives 107. In one or more embodiments the weight given to different objectives may be set by the user of the model selection system. Illustrative objectives 107 that may be considered in one or more embodiments may include for example, without limitation: selecting models designed for patient types that are similar to the patients in the target group; selecting models that predict risks for events that are similar to the events or diagnoses observed in the target patient group; selecting models that use inputs that are similar to those that are available for the target patient group; selecting models in a combination that target different physiological systems; selecting models that generate predicted event probabilities with distributions that are similar to those of the training datasets of the models; and selecting a combination of models that generate predicted event probabilities that are uncorrelated.

Selecting models designed for patient types that are similar to patients in the target group may be achieved using prior knowledge of the clinical team and administration regarding admitting practice. It may additionally be achieved by comparing distributions of individual features in the sample patient data to distributions of the same features in the model training dataset, for example, using the Kullback-Leibler divergence, Mahalanobis distances, or other distribution distance metrics.

Figure 2:
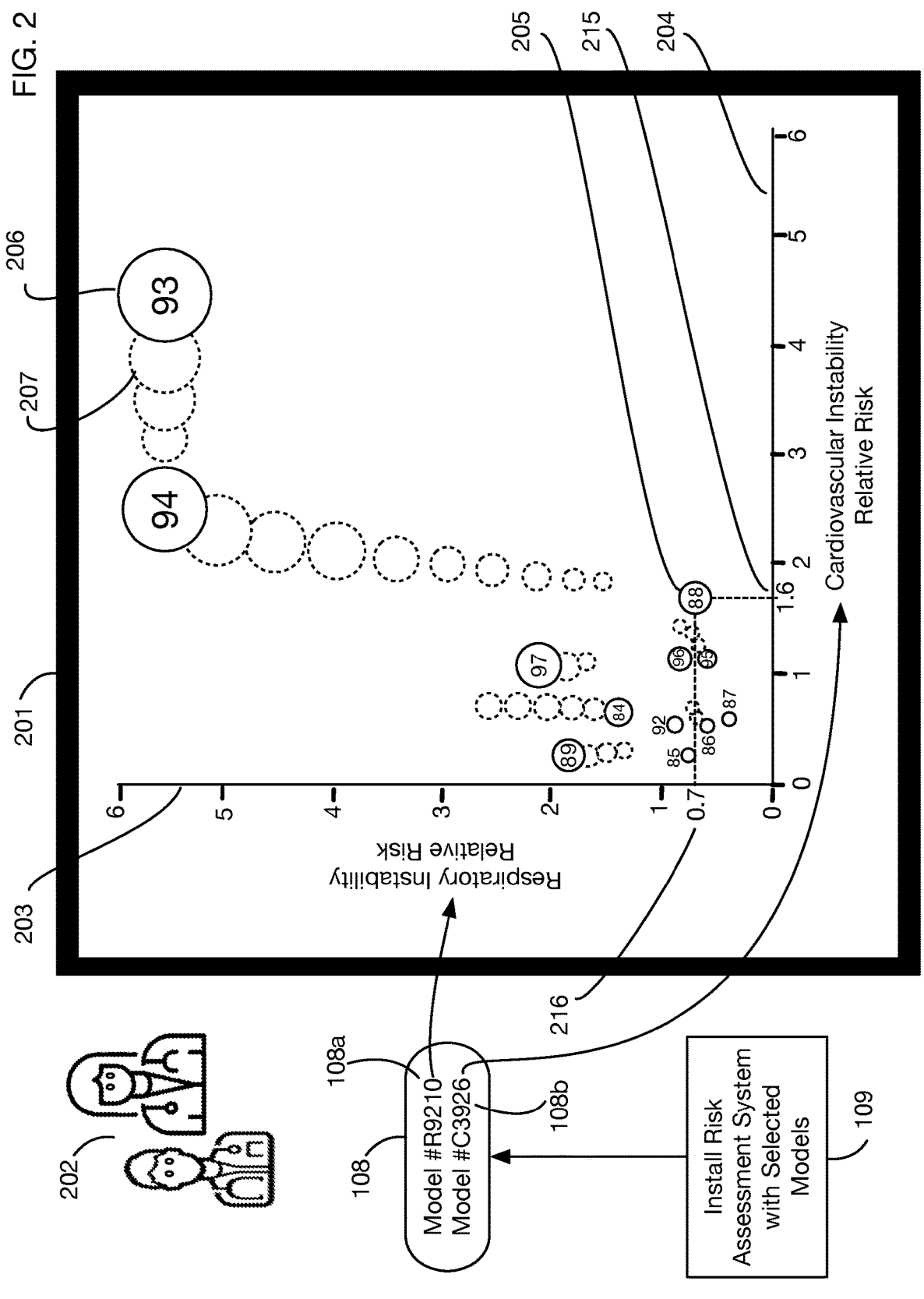
FIG. 2 shows an illustrative display of the patient risk prediction results for the deployed model combination selected by the system of FIG. 1.

The selected model combination 108 may be used in a patient risk assessment system that is installed to monitor patients in the target patient group 103. FIG. 2 shows an illustrative display 201 of the output of a such a risk assessment system that may be used by the medical professionals 202 of the unit to monitor their patients. The selected model combination 108 includes two different models 108*a* and 108*b*, so the risk assessment is two-dimensional. The event probability generated by each model is normalized to a relative risk (as described below), and the relative risk for each patient is plotted on two axes 203 and 204 that correspond to the two models 108*a* and 108*b*, respectively, in model combination 108. In this illustrative plot, each patient is identified by a bed number, and a circle with that bed number is shown at the current risk level (on the two axes) for that patient. For example, circle 205 shows the two-dimensional risk for the patient in bed number 88; the relative risk 215 for the cardiovascular model 108*b* in combination 108 is 1.6, and the relative risk 216 for the respiratory model 108*a* in combination 108 is 0.7.

Dotted circles show the recent history of the patient risk level, so that the staff 202 can see the evolution of each patient's risk. The size of each circle shows the total risk, which may be for example defined as the distance of the circle from the origin. For example, large circle 206 shows that the risk for patient in bed number 93 is very high, and dotted circle 207 shows that the risk for this patient is increasing.

The display 201 of patient risk levels is illustrative; one or more embodiments of the invention may display risks calculated by selected model combinations in any desired manner. Model combinations may be two-dimensional, as in FIG. 2, or they may have any number of dimensions. Displays of risk levels on more than two dimensions may use various methods to show the risk on each dimension; for example, multiple plots may be shown, or attributes such as color and size may be used to show additional dimensions. Alternatively, or in addition, axes may be the composite of multiple models that provide the desired information or improved predictions when used in combination.

Figure 3:
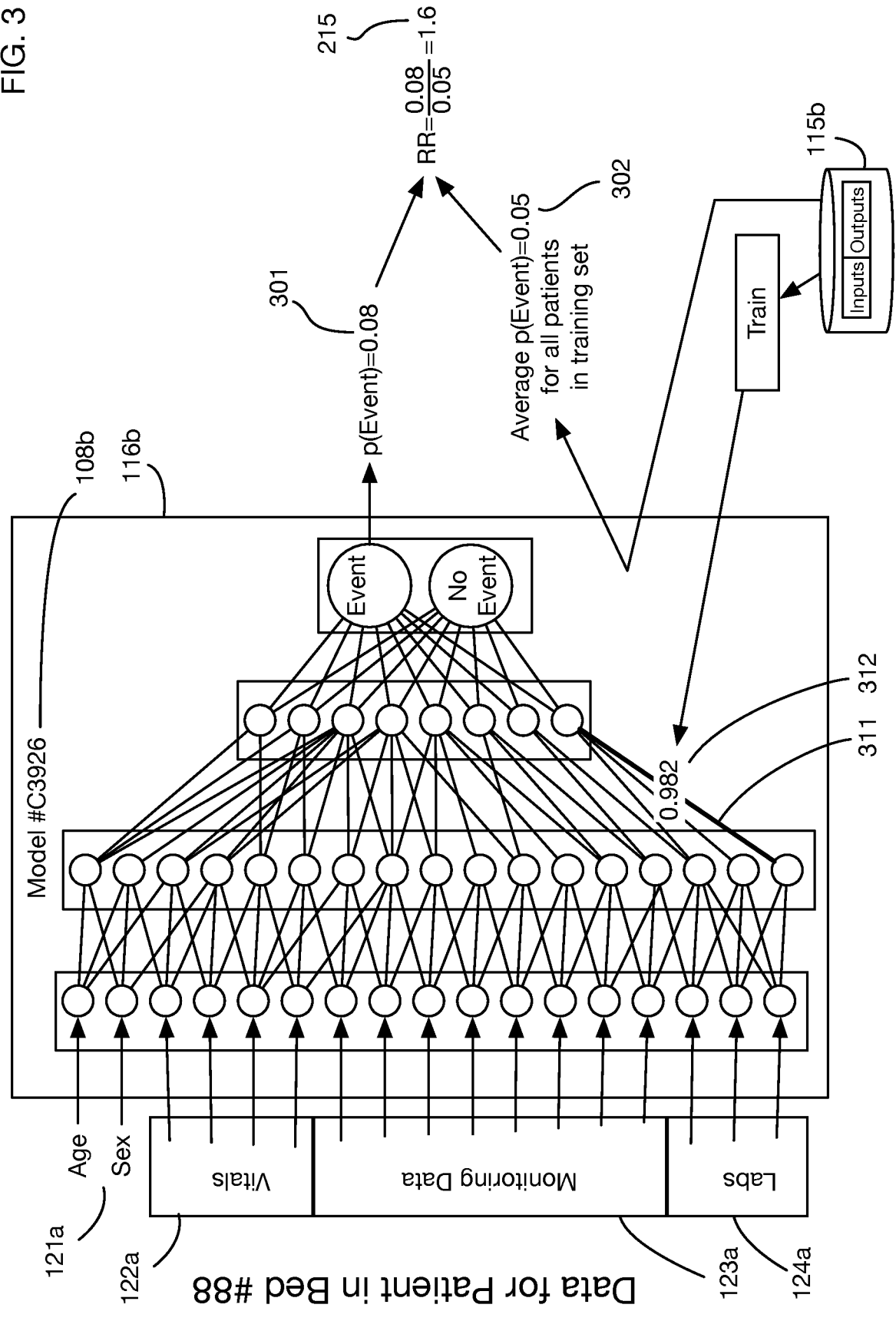
FIG. 3 shows an illustrative risk prediction model that uses a neural network to map from patient data to a risk probability.

FIG. 3 shows an illustrative calculation of the relative risk 215 for patient #88 in FIG. 2. Associated with the model 108*b* is a function 116*b*, which in this example is implemented by a neural network. One or more embodiments may use any type of function or algorithm to calculate event probabilities. In this example, the neural network function is trained on a training dataset 115*b* associated with the model 108*b*. This training process may for example set the weights associated with the links between nodes; for example, the training process sets the weight of link 311 to value 312. (Other links have similar weights that are not shown.) The trained function 116*b* is then applied to the inputs associated with patient #88 to calculate the risk for this patient. Inputs may include the patient's demographic data 121*a*, vital signs 122*a*, monitoring data 123*a*, and lab results 124*a*. The outputs of the neural network function 116*b* may be probabilities for the event or events predicted by the model. In this example the model is associated with a single event, and function 116*b* calculates event probability 301 for the patient. For ease of interpretation, this event probability 301 may be converted to a relative risk (RR) 215 by dividing it by the average probability 302 for all patients in the training dataset 115*b*. The average relative risk for the training dataset is therefore normalized to 1.0.

Figure 4:
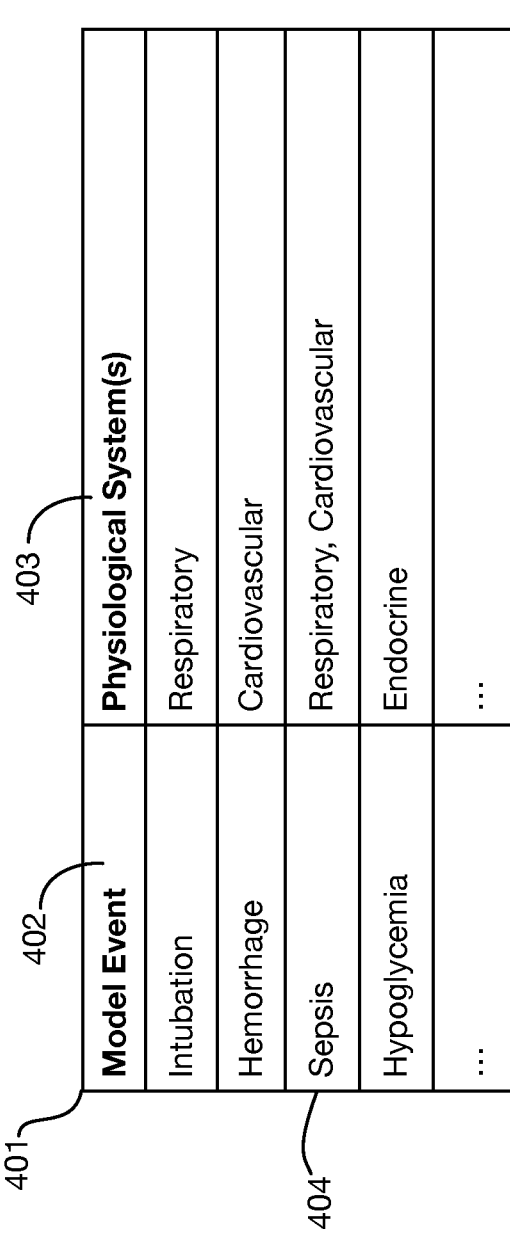
FIG. 4 shows illustrative risk prediction models and the physiological systems associated with each model.
Figure 5:
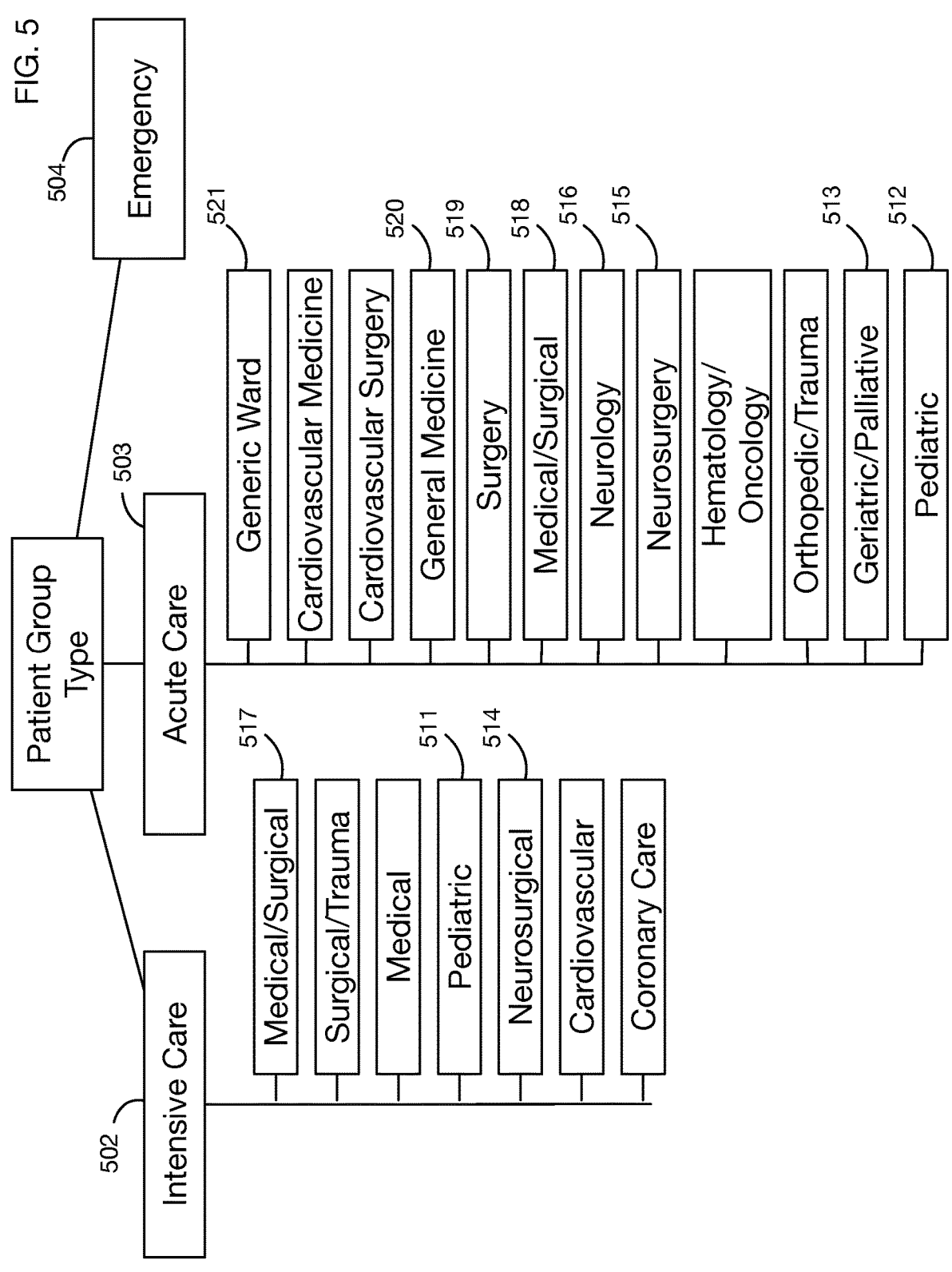
FIG. 5 shows illustrative patient group types that may be associated with each risk prediction model.

In addition to the event probability function, other information that may be associated with a model may include one or more physiological systems associated with the model's event, and characteristics of the patient group(s) on which the model is trained. FIG. 4 shows a partial table 401 with the physiological system or systems 403 associated with selected model events 402. Some events, such as sepsis 404, may be associated with multiple physiological systems. FIG. 5 shows an illustrative classification of patient types that may be associated with models. This hierarchical classification differentiates first among intensive care patients 502, acute care patients 503, and emergency care patients 504. Large health care facilities in particular may create specialized unit types or patient subgroups within these broad categories, as shown. Some patient group types, such as types 511, 512, and 513, may be specialized for certain age groups. Others such as patient types 514, 515, and 516, may be specialized for certain medical specialties. Some patient types such as 517, 518, 519, and 520, may be classified based on whether they contain medical patients, surgical patients, or both. Finally, a generic patient type 521 may include multiple types of patients, and the specifics of the patient mix may be unknown. (In these situations with target patient groups that are a mix of different patient subpopulations, an ensemble of models that are fit to those subpopulations may provide better overall risk prediction than any of these models individually.)

Figure 6:
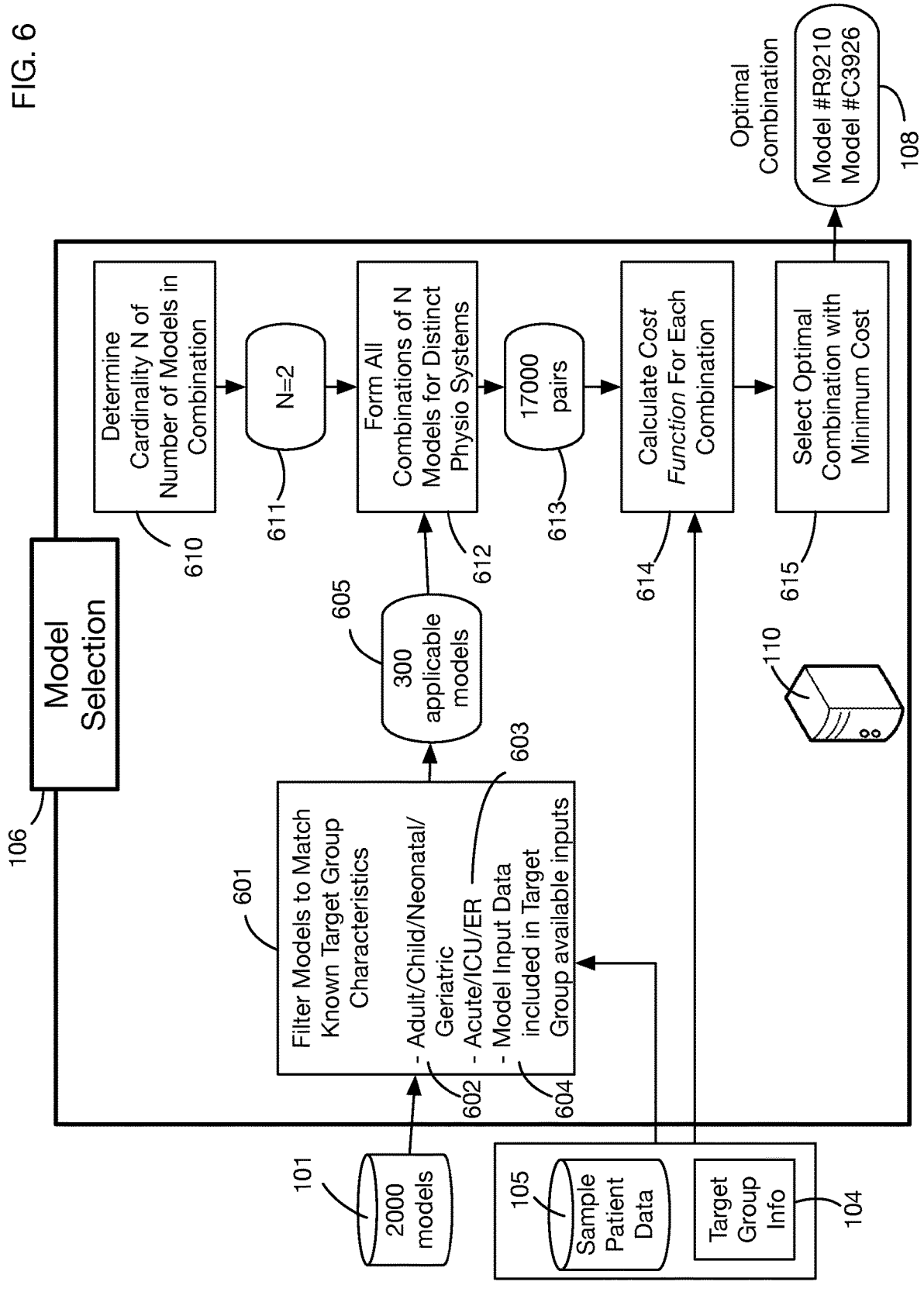
FIG. 6 shows a flowchart of illustrative steps performed by a model selection system to identify an optimal model combination for a target patient group.

Turning now to details of the model selection system 106, FIG. 6 shows an overview of illustrative steps that may be performed in one or more embodiments to determine an optimal model combination for a target patient group. Some or all of these steps may be executed by a processor or processors 110. A set of risk models 101 is input into the system 106, along with target patient group characteristics 104 and sample target patient data 105 (as described above), and an optimal model combination 108 is output. In a first filtering step 601, models 101 are compared to the target patient group data to exclude models that are unsuitable or that differ substantially from the target patient data. For example, filtering 601 may exclude models with a patient type that differs significantly from the target patient type. If the age group for a model is different from the target patient type age group, the model may be excluded by the filter; for example, a model for pediatric patients may be inappropriate for adult patients and vice versa. Similarly, in one or more embodiments a model may be excluded if for example it is a model for intensive care patients, but the target patient group is an acute care patients.

The filtering step 601 may also filter models 101 based on a comparison of the input data available from the target unit to the inputs required by the model. If the model's inputs are not available from the target unit, the model may be excluded from consideration (unless default values can be reasonably defined for the missing inputs). A model that predicts a myocardial infarction risk based on heart monitor data may be excluded from consideration from a target unit without heart monitors, for example. After filtering, the remaining applicable models 605 are considered for calculation of the optimal model combination.

Model combinations with any number of models (dimensions) may be considered for a target unit. A selection 610 of the combination cardinality (number of models) may be made before calculating an optimal combination with this number of models. A common choice of cardinality may be two, for example, for ease of display in a risk chart such as that shown in FIG. 2; however, combinations with any number of models may be considered. In one or more embodiments, multiple models may be reduced to a target dimension by calculating a composite risk score (for example via a weighted and normalized root mean square calculation). A next step 612 is to generate combinations of the filtered applicable models 605 with the desired number of dimensions. All possible combinations may be considered; however, to improve coverage of multiple body systems, combinations with multiple models that address the same physiological systems may be excluded. For example, combinations including a model for myocardial infraction and a model for hypotension might be excluded, since both models are related to the cardiovascular system. Alternatively, an ensemble model including both such models may be considered. After eliminating model combinations that address redundant physiological systems, the remaining model combinations 613 are ranked to find the optimal combination.

Ranking of model combinations may use a "cost function" calculated for each model combination in step 614. Conceptually a cost function may quantify how far a model combination deviates from some optimal values; for example, the cost function may measure the deviation between characteristics of the model combination and characteristics of the target patient group. An illustrative cost function is described below with respect to FIG. 7. After calculating the cost function for each combination 613, the combination with the lowest cost is selected in step 615 as the optimal model combination 108 for the target patient group.

FIG. 6 shows illustrative counts of the number of models and combinations that may be under consideration at each step. The actual counts will depend on the specific embodiment and the characteristics of the target patient group. In this example, 2000 models are in database 101, but only 300 applicable models remain after filtering step 601. With 2 models per combination as the selected combination cardinality in step 610, there are 300*299/2=44850 possible combinations of the 300 filtered applicable models; however, many of these may duplicate physiological systems. After excluding model combinations that address the same system, 17000 model combinations (with 2 models each) remain for ranking via the cost function; the lowest cost model among these 17000 is the output of the model selection system 106.

FIG. 7 shows an illustrative method to calculate a cost function 614 for each model combination under consideration. The illustrative cost function may be decomposed into multiple additive factors 702 shown in table 701; these factors correspond to the objectives 107 discussed with respect to FIG. 1. Table shows the optimal (lowest cost) value 703 for each factor, and a "distance metric" 705 for the factor that measures the deviation of a model combination from the optimal value 703. Associated with each factor may be a weight 704, which may be set as desired in each embodiment and application of the model selection system. The cost factors 711 through 715 of table 701 are illustrative; one or more embodiments may use any subset of these factors or may incorporate additional factors into a cost function.

Figure 8:
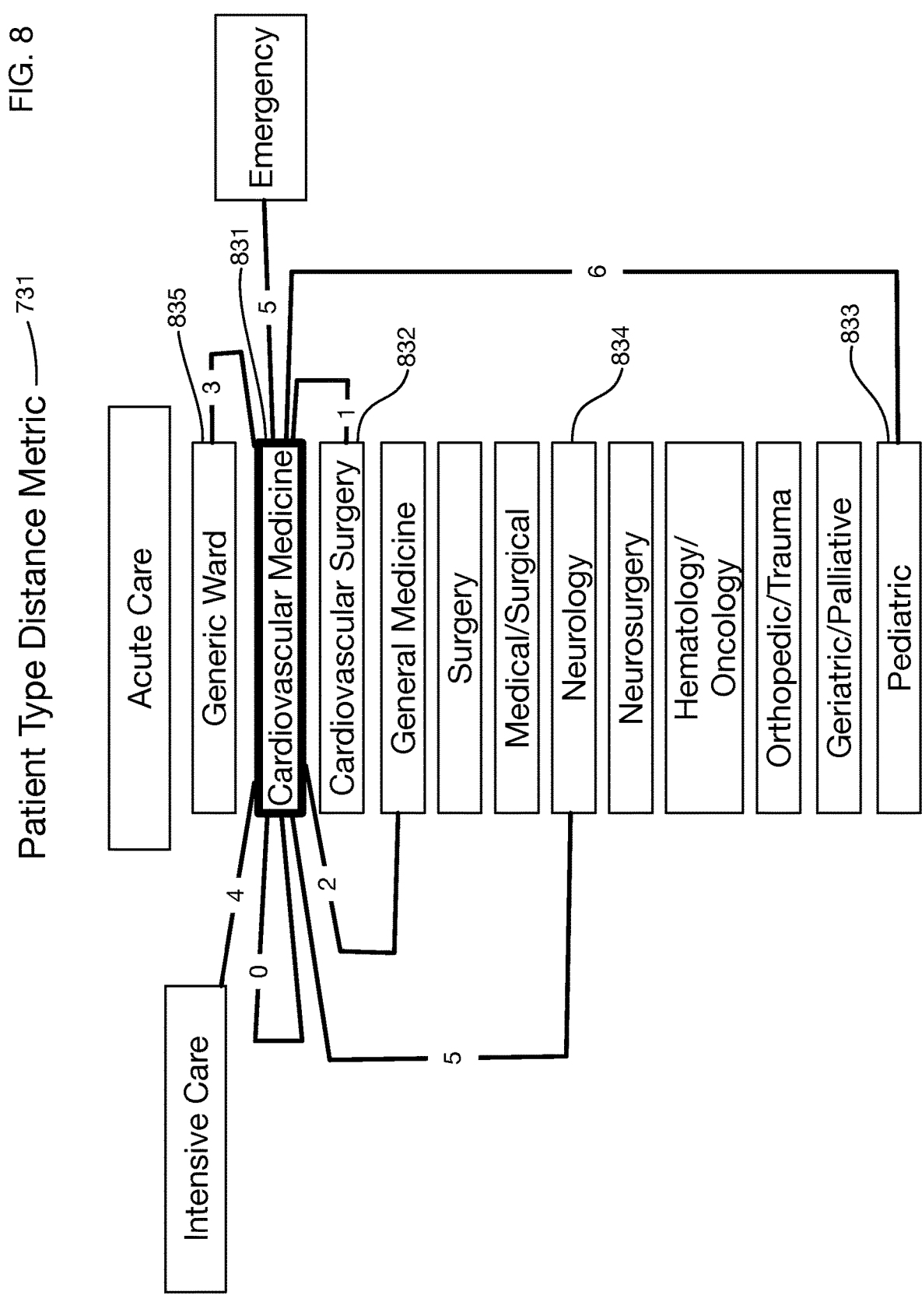
FIG. 8 shows an illustrative distance metric between a model's patient type and the patient type of a target patient group.

Factor 711 measures the differences between the patient types of the models of the combination and the patient type of the target patient group. The metric 731, which is illustrated in FIG. 8, may be applied to each model in the combination.

Figure 9:
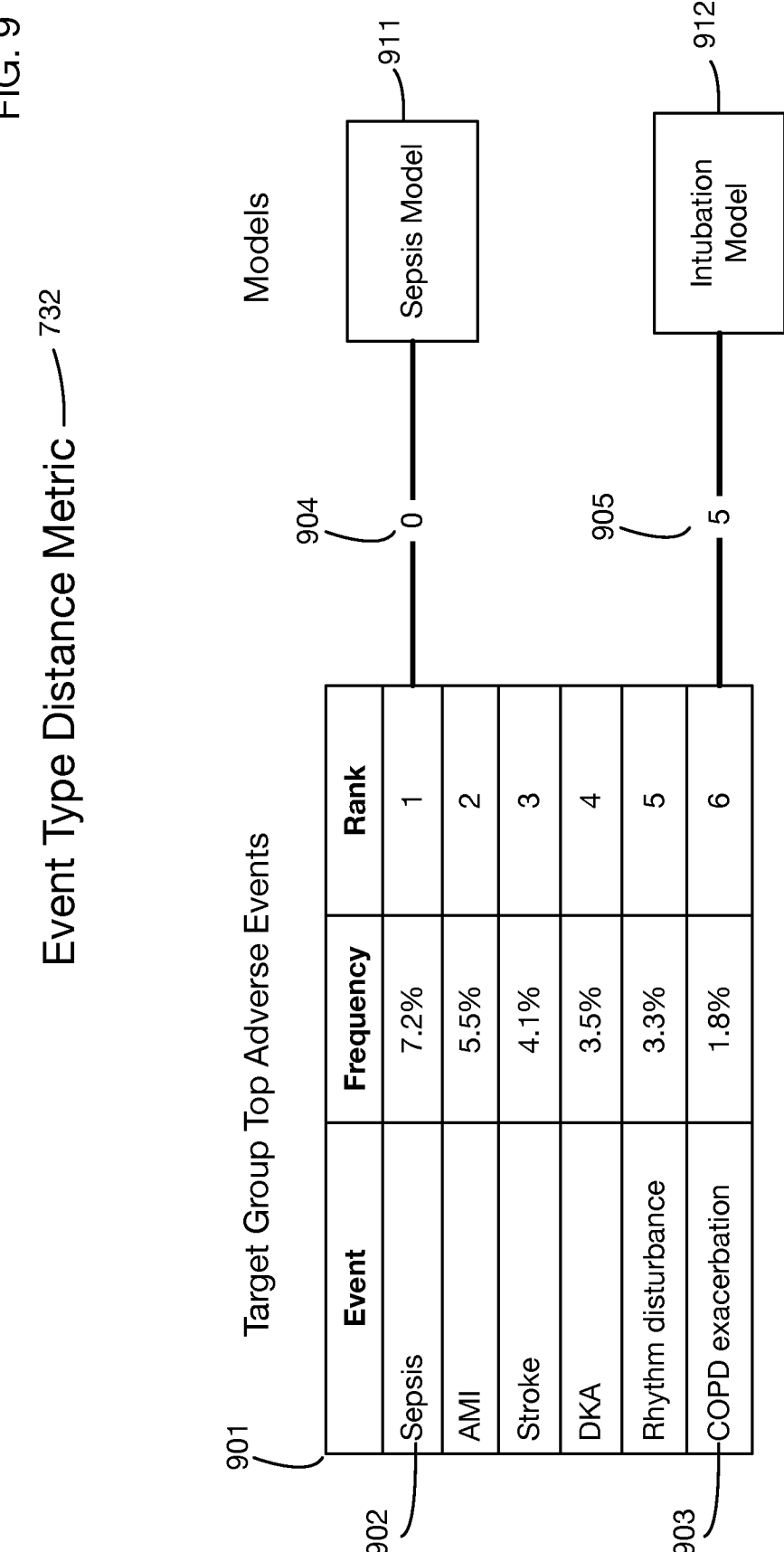
FIG. 9 shows an illustrative distance metric between a model's predicted event and the ranked adverse events that may occur in the target patient group.

Factor 712 measures the differences between the events associated with the models of the combination and the common events in the target patient group. The metric 732, which is illustrated in FIG. 9, may be applied to each model in the combination.

Factors 713 and 714 measure differences between the predicted risk distribution of the target patient group and desired features of this distribution. These differences may be measured for each model in the combination. The predicted risk distribution of the target patient group for a model may be calculated for example by applying the model function to the sample patient inputs for the sample obtained from the target patient group. (In one or more embodiments risks may be normalized as described below to a "relative risk" rather than an absolute probability of event occurrence.) One or more cost factors may be calculated in any desired manner from the predicted risk distribution of the target patient group. An illustrative method of calculating a cost factor from this predicted risk distribution is to calculate a statistic from the predicted risk distribution, and to measure the difference between this statistic and some desired optimal value for the statistic in the target patient group. The desired value for the statistic may be a fixed constant value, or it may be based on applying the same statistic to the risk distribution of the model's training dataset. Illustrative statistics that may be used in cost factors may include for example, without limitation, mean, median, quartiles, percentiles, ranges, variances or standard deviations, entropies, divergences, or any other function of a distribution.

Figure 10:
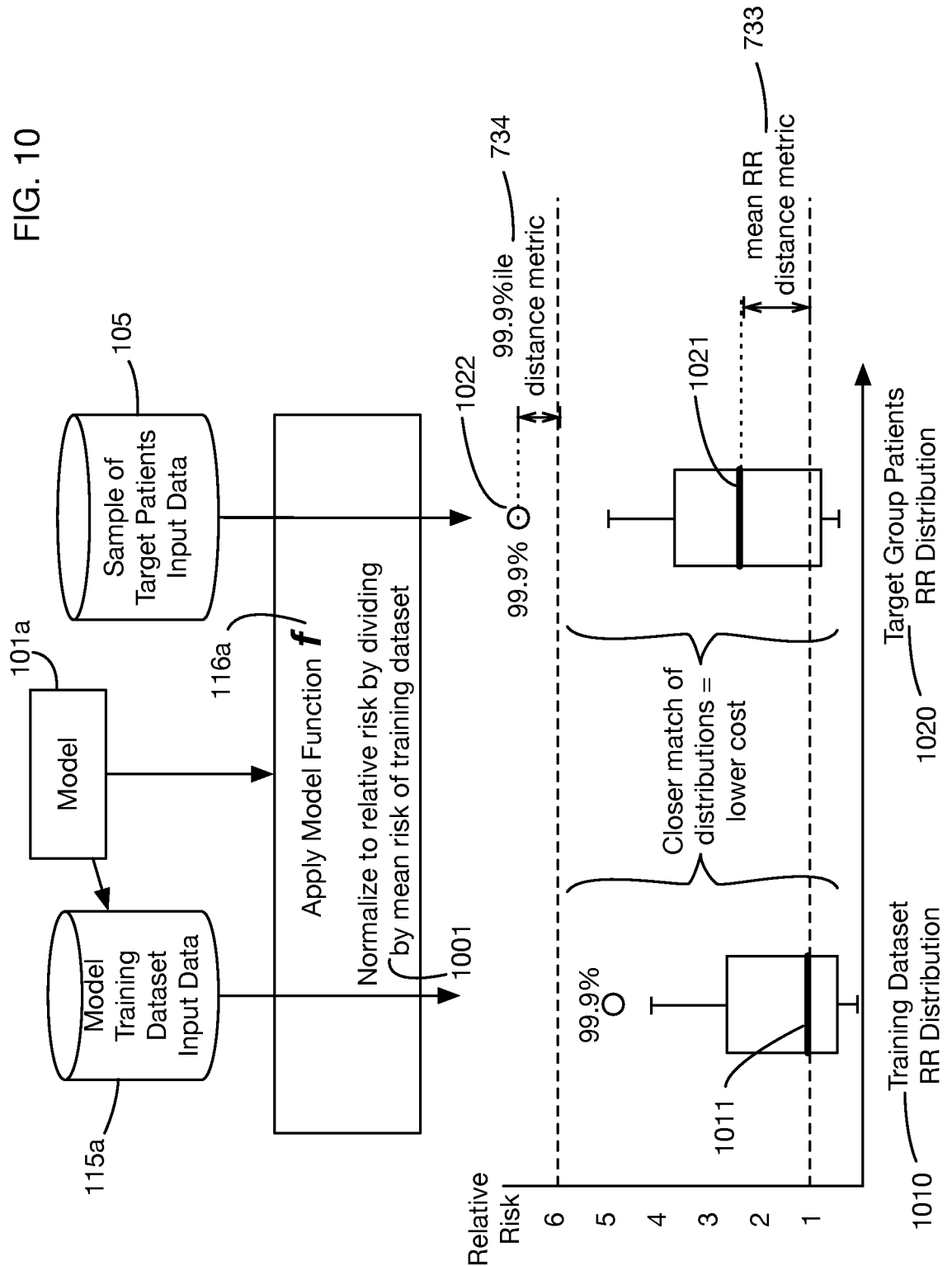
FIG. 10 shows illustrative distance metrics between the predicted risk distribution for a model's training set and the predicted risk distribution for a target patient group.

Factor 713 measures the differences between the mean value of the predicted distribution of relative risk for each model and the corresponding mean value of predicted relative risk for the model's training dataset. The metric 733, which is illustrated in FIG. 10, may be applied to each model in the combination.

Factor 714 measures the differences between the ranges of the predicted distributions (as measured for example by the 99.9th percentile values) and a desired range that effectively separates high and low risk patients. The cost factor is based on the difference between the 99.9th percentile statistic applied to the predicted risk distribution for the target group and a desired maximum value of a risk display range. For illustrative factor 714 and associated illustrative metric 734, this maximum value is 6.0. The metric 734, which is illustrated in FIG. 10, may be applied to each model in the combination.

Figure 11:
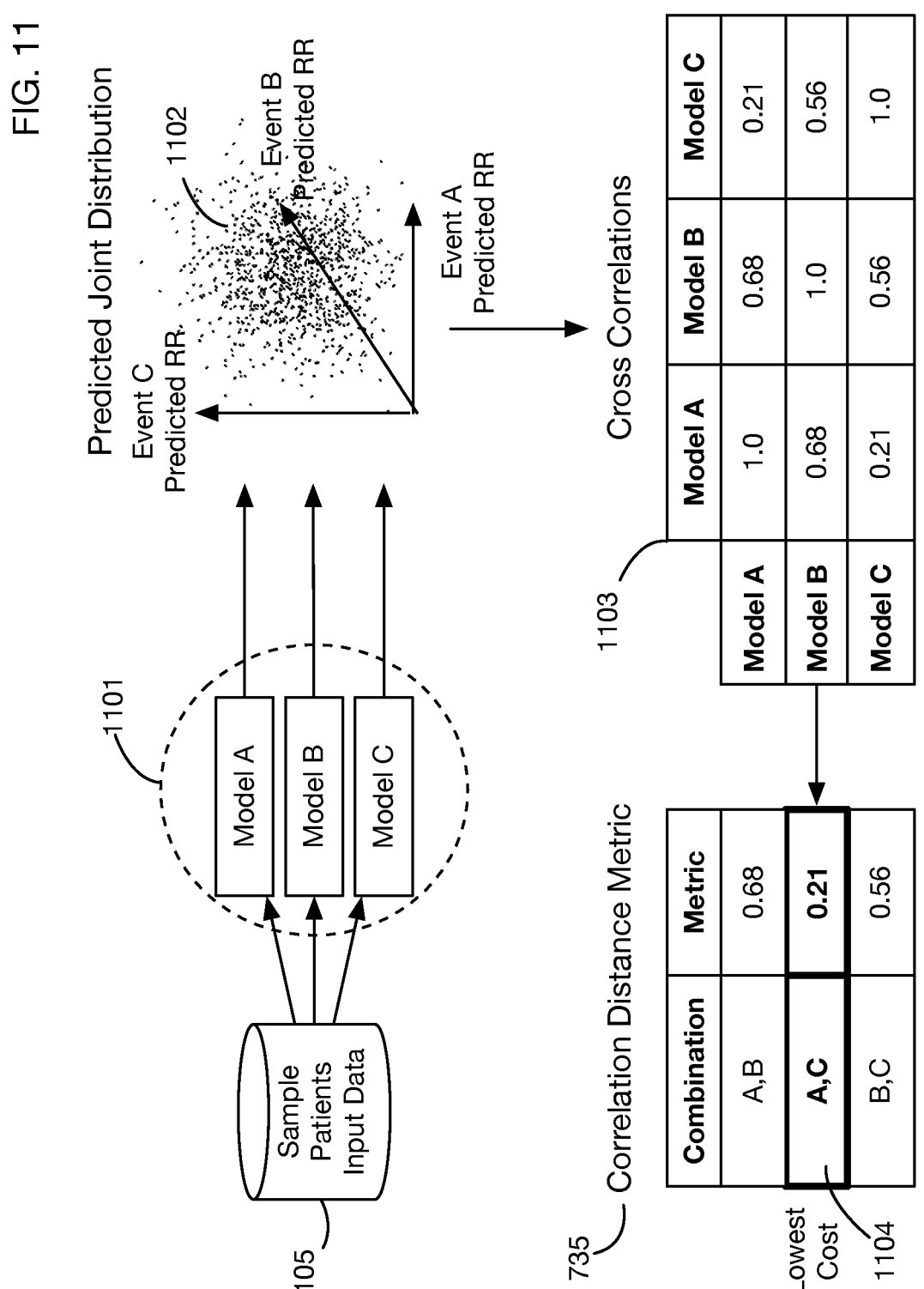
FIG. 11 shows an illustrative distance metric based on cross-correlations between risk distributions of different models.

Factor 715 measures the difference between the observed cross-correlation of the models in a combination and an ideal value of no correlation (or negative correlation). The metric 735, which is illustrated in FIG. 11, may be applied to the pairs in the model combination.

Formula 721 shows an illustrative calculation of a cost function from the factors 702. This illustrative cost function is a weighted sum of the squared distances between each factor value and the optimal value 703, using the distance metrics 705 and the weights 704. The cost function may be calculated for each model combination in the set 613. The optimal model combination is then obtained in step 615 by minimizing the cost function over the set of model combinations.

The factors and distance metrics in table 701 are illustrative; one or more embodiments may use different factors and may calculate factor costs in any desired manner. Costs associated with individual factors may also be combined into a total cost function in any desired manner, including but not limited to using a weighted sum of squared distances as illustrated in formula 721. Additional factors may include for example, without limitation, either or both of an entropy factor and an input distribution similarity factor. An entropy factor may for example include an entropy estimate (at a relevant scale or multiscale) for each model in the combination, which measures how smooth the model estimated risks are relative to the estimated risks in the training set. An input distribution similarity factor may compare distributions of individual features in the sample patient data to distributions of the same features in the model training dataset for each model in the combination, for example, using the Kullback-Leibler divergence, Mahalanobis distances, or other distribution distance metrics.

FIGS. 8, 9, 10, and 11 illustrate the distance metrics 705 for the factors 702. FIG. 8 shows selected values for an illustrative distance metric 731 that measures the similarity of patient types. Illustrative distances are shown between patient type 831 (cardiovascular medicine) and selected other patient types. These values are for illustration only; one or more embodiments may measure distances between patient types with any desired values. For the embodiment shown in FIG. 8, the distance metric between patient type 831 and itself is 0 since this represents a perfect match. Patient type 832 is closely related to patient type 831 since both are patients with cardiovascular conditions, so the distance is set to 1. Patient type 834 is at a greater distance 5 from patient type 831 since it is concerned with a different physiological system. Patient type 833 is at a higher distance 6 from patient type 831 since it includes pediatric patients while patient type 831 includes adult patients. Patient type 835 is at a medium distance 3 from patient type 831 since it contains a mix of all patient types, including potentially cardiovascular patients.

FIG. 9 shows illustrative values for an event type distance metric 732, which may measure for example a distance between an event associated with a model and an event in the target patient. For this illustrative metric, the "distance" between a model and a target patient group is based on the frequency of the model's event occurring in the target patient group, compared to other types of events. For a target patient group where the model's event is the target group's most common event, the distance metric is zero. As the event becomes less common in the target patient group, the distance metric increases. For example, table 901 shows an illustrative rank-ordered list of the most common events in the target patient group. (The events of interest here are generally those that occur after admission. For example, a care unit could have 50% sepsis diagnoses because everyone with sepsis goes there for care, but that is present on admission and would not be included in the relevant event frequency as discussed here. The events of interest represent clinical deterioration post-admission, like respiratory failure requiring intubation, bleeding leading to transfusion, or possibly septic shock requiring vasopressors.)

Since sepsis 902 is the most common observed event in this unit, the distance 904 between this target patient group and a sepsis model 911 is 0. For an intubation model 912, the event that is most closely related to intubation is COPD exacerbation 903. Since this event is ranked 6th in the target patient group in frequency, the distance 905 between the target patient group and this model is 5 (which is the rank 6 minus 1). In one or more embodiments the distance metric related to the model's event may be based on the absolute frequency of the event in the target patient group, rather than the relative rank. For example, if the frequency of the event among the target patients is f, an illustrative distance metric may be d (event, target group)=1/f-1; this metric assigns a zero metric (lowest cost) for an event that occurs in all patients, and a very high metric as the frequency of the event in the target patient group approaches zero.

FIG. 10 illustrates distance metrics based on the predicted risk distribution of a model 101*a* in the target patient group. As described with respect to FIG. 1, sample patient data 105 may be collected from the target patient group. This data may not include the actual occurrence of the model's event among the target group patients, but it may contain the input data, such as vital signs or bedside monitoring, that the model uses to predict the probability of the event occurring. It may therefore be possible to apply the model's function 116*a* to this target group input data 105 to determine a predicted event probability for each of the target group sample patients. Although data may not exist to compare this predicted probability to actual event occurrences in the target patient group, the overall distribution of predicted probabilities may be evaluated against desired distribution parameters. FIG. 10 shows distance metrics based on two statistics that may be calculated from the predicted target group risk distribution: metric 733 compares the mean of the predicted distribution to the mean of the corresponding distribution of the model's training dataset, and metric 734 compares the range (as represented by the 99.9th percentile value) to a desired value.

As illustrated in FIG. 10, the predicted distribution of risk for a model 101*a* is calculated by applying the model's function 116*a* to the sample patient input data 105 for the sample patients of the target patient group. To simplify comparisons and analyses, these absolute risks (event probabilities) may be converted into relative risks in step 1001 by dividing each event probability by the mean probability of the event in the model's training dataset. The resulting predicted relative risk distribution 1020 is shown in FIG. 10 as a boxplot. Applying the same function 116*a* and normalization 1001 to the model's training dataset 115*a* results in distribution 1010. The mean relative risk 1011 of the training dataset distribution 1010 is 1.0 by definition. The mean relative risk 1021 of the predicted target patient group relative risk (normalized to the mean of the training dataset) differs from the baseline 1011 by distance 733, which is the distance metric for factor 713. This metric is zero (lowest cost) when the predicted distribution for the target patient group matches the training dataset distribution in mean. One or more embodiments may compare the distributions 1010 and 1020 in any desired manner to form one or more distance metrics that measure how closely the predicted distribution matches that of the training dataset. In addition to or instead of comparing means, one or more embodiments may compare any statistics such as medians, quantiles, standard deviations, or entire distributions using metrics such as a Bhattacharyya distance or Kullback-Leibler divergence.

Another desired feature of the predicted distribution 1020 is that the predicted range of values correspond to a range that allows the medical professionals to effectively differentiate between low-risk and high-risk patients with sufficient resolution. Such range may be built into the risk prediction display and therefore impacts model selection. For example, the inventors have found that in some embodiments displaying a range of relative risk from 0.0 to 6.0 (as in the plot of FIG. 2) provides good resolution between lower risk and higher risk patients; therefore, distributions that fit within this range are preferred. Metric 734 therefore measures the difference between the 99.9th percentile statistic 1022 of the predicted relative risk and the desired maximum value of the risk display range, such as 6.0. (The maximum value of the risk display range may vary across embodiments and may depend for example on the user interface for the display of relative risks and on the distribution of relative risks for the target patient group.) Using the 99.9th percentile instead of the absolute maximum allows some extreme outliers to exceed the target upper value (which may be the maximum of the risk display range), while ensuring that almost all of the predicted relative risks fit within the desired range.

FIG. 11 illustrates a distance metric 735 based on the correlation between predicted risks from different models in a model combination. A simplified scenario is shown that considers combinations of two models selected from three models 1101. As in FIG. 10, the risk prediction functions of each of the models 1101 are applied to the input data 105 from the target patient group to calculate a joint distribution 1102 of relative risks for the three events associated with the three models 1101. From this joint distribution 1102, cross correlations 1103 are calculated for each pair of models. These correlations may be used directly as the correlation distance metric 735 for combinations of two models, or the distance metric may be any desired function of the correlations among models in a combination. The ideal model combination uses models that are uncorrelated, which corresponds to a distance metric of zero. In the example shown in FIG. 11, the lowest cost model combination 1104 (on the cross correlation factor) is the combination with the lowest correlation between the two models in the combination.

While the invention herein disclosed has been described by means of specific embodiments and applications thereof, numerous modifications and variations could be made thereto by those skilled in the art without departing from the scope of the invention set forth in the claims.

What is claimed is:

1. A system that selects an optimal model combination to predict patient risks, comprising:

a database comprising a multiplicity of risk models, wherein each risk model of said multiplicity of risk models comprises an event;

one or more physiological systems associated with said event;

a patient type;

one or more inputs;

a function that maps values of said one or more inputs to a probability of occurrence of said event in patients of said patient type, wherein said each risk model predicts the probability of occurrence of said event over a specified timeframe, wherein said each risk model calculates the probability of occurrence of said event from said one or more inputs and from calculated features, wherein said function is derived using a machine learning method applied to a training dataset, wherein said machine learning method comprises one or more of regression, restricted cubic spine regression, neural networks, decision trees, bagged or boosted decision trees; and training samples, wherein each training sample of said training samples comprises training sample input values of said one or more inputs; and a training sample output value of an occurrence of said event;

target patient group data associated with a target patient group, said target patient group data comprising a target patient type;

target patient available inputs;

target patient samples, wherein each target patient sample of said target patient samples comprises target patient sample input values of said target patient available inputs;

a processor coupled to said database and to said target patient group data, wherein said processor comprises a server, a computer, a mobile device, an application-specific integrated circuit or a network of a combination thereof, wherein said processor is configured to execute a model selection system to execute a procedure that filters said multiplicity of risk models to identify applicable risk models by comparing said multiplicity of risk models to said target patient group data and therefrom to exclude models that differ from said target patient group data, to optimize model risk prediction for said event, including a different target patient type, inputs unavailable in the target patient available inputs;

such that after said filters, remaining models that are not excluded from said multiplicity of risk models are considered as said applicable risk models to calculate an optimal model combination, selects a model combination cardinality comprising an integer greater than or equal to two;

generates all relevant combinations of said applicable risk models, wherein each combination of said all relevant combinations has a number of models in said each combination equal to said model combination cardinality; and different models in said each combination have different associated one or more physiological systems, such that model combinations that address a redundant physiological system are eliminated;

applies a cost function to each combination of said all relevant combinations to calculate an associated combination cost to rank said each combination of said all relevant combinations, wherein said cost function measures a difference between said each combination and an optimal combination for said target patient group data to quantify how far said each combination deviates from optimal values of said optimal combination;

generates and identifies a selected combination of said all relevant combinations having a lowest associated combination cost, from said cost function that is applied, as an optimal model combination for said target patient group data;

selects said optimal model combination that is generated based on a set of objectives;

installs said optimal model combination that is generated in a patient risk assessment system and outputs a display of said optimal model combination on a user interface to monitor said patients, wherein said set of objectives are set by a user of the model selection system, wherein said selected combination is multi-dimensional, wherein said display comprises multiple plots comprising a plot of risk levels for each patient of said patients displaying a risk on each dimension of said selected combination that is multi-dimensional, or attributes comprising color and size used to show additional dimensions of said selected combination that is multi-dimensional, wherein said patient risk assessment system continually or periodically monitors patients in the target patient group for risks associated with each model using the selected combination that is multi-dimensional, wherein said procedure is repeated periodically or as needed as additional data is collected on the target patient group, such that over time each cost function that is applied from said procedure that is repeated is used to monitor how well the optimal model combination that is generated and selected fits the target patient group over time, to train said function of said each risk model using the training dataset, wherein said optimal model combination is utilized to adjust care of said patients based on risks predicted by said optimal model combination, the risks comprising predicted probabilities of adverse clinical events derived from the cost function and model functions applied to said target patient group data, such that said optimal model combination identifies patients at elevated risk for said events and enables risk-based clinical actions comprising at least transfer of a patient of said patients to an Intensive Care Unit (ICU), modification of treatment, or discharge of said patient from a hospital.

2. The system that selects an optimal model combination to predict patient risks of claim 1, wherein in each applicable risk model of said applicable risk models said target patient available inputs contains said one or more inputs associated with said each applicable risk model; and said target patient type contains said patient type associated with said each applicable risk model.

3. The system that selects an optimal model combination to predict patient risks of claim 1, wherein said cost function comprises a weighted sum of cost factors.

4. The system that selects an optimal model combination to predict patient risks of claim 3, wherein said cost factors comprise a predicted risk distribution difference factor for each model of said each combination.

5. The system that selects an optimal model combination to predict patient risks of claim 4, wherein said predicted risk distribution difference factor associated with each model is based on a difference between a statistic applied to a predicted target patient group risk distribution and a desired value of said statistic.

6. The system that selects an optimal model combination to predict patient risks of claim 5, wherein said statistic comprises one or more of a mean, a percentile, an entropy, an entropy rate, and a distribution divergence.

7. The system that selects an optimal model combination to predict patient risks of claim 5, wherein said predicted target patient group risk distribution comprises a distribution of output values of said function applied to said target patient sample input values, divided by a mean value of training sample output values associated with each model.

8. The system that selects an optimal model combination to predict patient risks of claim 7, wherein said desired value of said statistic comprises said statistic applied to a training set risk distribution; and said training set risk distribution comprises a distribution of training sample output values associated with each model, divided by a mean value of said training sample output values associated with each model.

9. The system that selects an optimal model combination to predict patient risks of claim 8, wherein said statistic comprises a mean.

10. The system that selects an optimal model combination to predict patient risks of claim 7, wherein said statistic comprises a 99.9th percentile; and, said desired value of said statistic comprises a maximum of a risk display range.

11. The system that selects an optimal model combination to predict patient risks of claim 7, wherein said cost factors further comprise an outputs correlation factor across models of said each combination.

12. The system that selects an optimal model combination to predict patient risks of claim 11, wherein said outputs correlation factor across models of said each combination comprises a correlation coefficient between said predicted target patient group risk distribution across said models of each combination.

13. The system that selects an optimal model combination to predict patient risks of claim 3, wherein said cost factors further comprise a patient type difference factor for each model of said each combination based on a difference between said patient type associated with said each model and said target patient type.

14. The system that selects an optimal model combination to predict patient risks of claim 3, wherein said cost factors further comprise an event frequency factor for each model of said each combination that measures how frequently said event associated with said each model occurs in said target patient group data.

15. The system that selects an optimal model combination to predict patient risks of claim 9, wherein in each applicable risk model of said applicable risk models said target patient available inputs contains said one or more inputs associated with said each applicable risk model; and said target patient type contains said patient type associated with said each applicable risk model; and, said cost factors further comprise an outputs correlation factor across models of said each combination comprising a correlation coefficient between said predicted target patient group risk distribution across said models of each combination;

a patient type difference factor for each model of said each combination based on a difference between said patient type associated with said each model and said target patient type; and, an event frequency factor for each model of said each combination that measures how frequently said event associated with said each model occurs in said target patient group data.

16. The system that selects an optimal model combination to predict patient risks of claim 3, wherein said cost factors further comprise an entropy factor for each model of said each combination that measures how smooth a predicted target patient group risk distribution associated with said each model is relative to a training set risk distribution of said each model.

17. The system that selects an optimal model combination to predict patient risks of claim 3, wherein said cost factors further comprise an input distribution similarity factor for each model of said each combination that measures a difference between distributions of features in said target patient sample input values and distributions of said features in said training sample input values.

\* \* \* \* \*